(12) United States Patent
Clemens et al.

(10) Patent No.: US 7,641,857 B2
(45) Date of Patent: Jan. 5, 2010

(54) MEASURING APPARATUS USED FOR DETERMINING AN ANALYTE IN A LIQUID SAMPLE, COMPRISING POLYMER ELECTRONIC COMPONENTS

(75) Inventors: Wolfgang Clemens, Puschendorf (DE); Axel Gerlt, Furth (DE); Bernd Rosicke, Mannheim (DE)

(73) Assignee: PolyIC GmbH & Co. KG, Furth (DE)

( * ) Notice: Subject to any disclaimer, the term of this patent is extended or adjusted under 35 U.S.C. 154(b) by 656 days.

(21) Appl. No.: 10/534,678

(22) PCT Filed: Nov. 14, 2003

(86) PCT No.: PCT/DE03/03784

§ 371 (c)(1),
(2), (4) Date: Nov. 10, 2005

(87) PCT Pub. No.: WO2004/044571

PCT Pub. Date: May 27, 2004

(65) Prior Publication Data

US 2006/0121625 A1  Jun. 8, 2006

(30) Foreign Application Priority Data

Nov. 14, 2002  (DE) ................................ 102 53 154

(51) Int. Cl.
*G01N 27/00* (2006.01)
*G01N 21/00* (2006.01)

(52) U.S. Cl. .............. 422/82.01; 422/82.02; 422/82.05; 422/50; 422/55; 422/56; 422/58; 422/61; 422/68.1; 436/169; 436/170; 436/86; 436/69

(58) Field of Classification Search ................. 436/169, 436/69, 86, 170; 422/63, 82.02, 82.05, 50, 422/55, 56

See application file for complete search history.

(56) References Cited

U.S. PATENT DOCUMENTS 3,512,052 A   5/1970  MacIver et al.

(Continued)

FOREIGN PATENT DOCUMENTS

DE     33 38 597     5/1985

(Continued)

OTHER PUBLICATIONS

Assadi A, et al:, Field-Effect Mobility of Poly (3-Hexylthiophene) Dept. of Physics and Measurement Technology, Received Mar. 3, 1988; accepted for Publication May 17, 1988.

(Continued)

*Primary Examiner*—Tony G Soohoo
*Assistant Examiner*—Robert Eom
(74) *Attorney, Agent, or Firm*—Carella Byrne et al.; Elliot M. Olstein; William Squire (57) ABSTRACT

A measuring apparatus for determining an analyte in a liquid sample includes the following apparatus components: a test element with a test field for applying the liquid sample, the test element experiencing a detectable modification due to the analyte to be determined, a detector which detects the modification and generates an electrical detector signal as a function of it, an evaluation circuit arranged downstream of the detector, which evaluates the detector signal to form a measurement result, a display device connected to the evaluation circuit for displaying the measurement result, and an electrical power supply for supplying electrical power to the electrical apparatus components. At least some of the electrical apparatus components are formed on the basis of polymer electronics so that the analyte can be determined straightforwardly, conveniently and inexpensively.

17 Claims, 3 Drawing Sheets

U.S. PATENT DOCUMENTS

| | | | |
|---|---|---|---|
| 3,769,096 A | 10/1973 | Ashkin | |
| 3,955,098 A | 5/1976 | Kawamoto | |
| 4,302,648 A | 11/1981 | Sado et al. | |
| 4,340,657 A | 7/1982 | Rowe | |
| 4,442,019 A | 4/1984 | Marks | |
| 4,865,197 A | 9/1989 | Craig | |
| 4,926,052 A | 5/1990 | Hatayama | |
| 5,173,835 A | 12/1992 | Cornett et al. | |
| 5,206,525 A | 4/1993 | Yamamoto et al. | |
| 5,259,926 A | 11/1993 | Kuwabara et al. | |
| 5,311,426 A * | 5/1994 | Donohue et al. | 422/102 |
| 5,321,240 A | 6/1994 | Takihira | |
| 5,344,501 A * | 9/1994 | Hashimoto et al. | 136/259 |
| 5,347,144 A | 9/1994 | Garnier et al. | |
| 5,364,735 A | 11/1994 | Akamatsu et al. | |
| 5,395,504 A | 3/1995 | Saurer et al. | |
| 5,480,839 A | 1/1996 | Ezawa et al. | |
| 5,486,851 A | 1/1996 | Gehner et al. | |
| 5,502,396 A | 3/1996 | Desarzens | |
| 5,546,889 A | 8/1996 | Wakita et al. | |
| 5,569,879 A | 10/1996 | Gloton et al. | |
| 5,574,291 A | 11/1996 | Dodabalapur et al. | |
| 5,578,513 A | 11/1996 | Maegawa | |
| 5,580,794 A | 12/1996 | Allen | |
| 5,629,530 A | 5/1997 | Brown et al. | |
| 5,630,986 A | 5/1997 | Miller | |
| 5,652,645 A | 7/1997 | Jain | |
| 5,691,089 A | 11/1997 | Smayling | |
| 5,729,428 A | 3/1998 | Sakata et al. | |
| 5,854,139 A | 12/1998 | Kondo et al. | |
| 5,869,972 A | 2/1999 | Birch et al. | |
| 5,892,244 A | 4/1999 | Tanaka et al. | |
| 5,946,551 A | 8/1999 | Dimitrakopoulos | |
| 5,967,048 A | 10/1999 | Fromson et al. | |
| 5,970,318 A | 10/1999 | Choi et al. | |
| 5,973,598 A | 10/1999 | Beigel | |
| 5,997,817 A | 12/1999 | Crismore et al. | |
| 6,036,919 A | 3/2000 | Thym et al. | |
| 6,045,977 A | 4/2000 | Chandross et al. | |
| 6,046,051 A * | 4/2000 | Jina | 436/69 |
| 6,060,338 A | 5/2000 | Tanaka et al. | |
| 6,083,104 A | 7/2000 | Choi | |
| 6,087,196 A | 7/2000 | Sturm et al. | |
| 6,133,835 A | 10/2000 | DeLeeuw et al. | |
| 6,150,668 A | 11/2000 | Bao et al. | |
| 6,197,663 B1 | 3/2001 | Chandross et al. | |
| 6,207,472 B1 | 3/2001 | Calligari et al. | |
| 6,215,130 B1 | 4/2001 | Dodabalapur | |
| 6,221,553 B1 | 4/2001 | Wolk et al. | |
| 6,251,513 B1 | 6/2001 | Hyatt | |
| 6,284,562 B1 | 9/2001 | Batlogg et al. | |
| 6,300,141 B1 | 10/2001 | Segal et al. | |
| 6,321,571 B1 | 11/2001 | Themont et al. | |
| 6,322,736 B1 | 11/2001 | Bao | |
| 6,329,226 B1 | 12/2001 | Jones et al. | |
| 6,330,464 B1 | 12/2001 | Colvin et al. | |
| 6,335,539 B1 | 1/2002 | Dimitrakopoulos et al. | |
| 6,340,822 B1 | 1/2002 | Brown et al. | |
| 6,344,662 B1 | 2/2002 | Dimitrakopoulos et al. | |
| 6,362,509 B1 | 3/2002 | Hart | |
| 6,403,396 B1 | 6/2002 | Gudesen et al. | |
| 6,429,450 B1 | 8/2002 | DeLeeuw et al. | |
| 6,498,114 B1 | 12/2002 | Amundson et al. | |
| 6,517,955 B1 | 2/2003 | Jacobsen et al. | |
| 6,555,840 B1 | 4/2003 | Hudson et al. | |
| 6,593,690 B1 | 7/2003 | McCormick et al. | |
| 6,603,139 B1 | 8/2003 | Tessler et al. | |
| 6,621,098 B1 | 9/2003 | Jackson et al. | |
| 6,852,583 B2 | 2/2005 | Bernds et al. | |
| 6,903,958 B2 | 6/2005 | Bernds et al. | |
| 2002/0018911 A1 | 2/2002 | Bernius et al. | |
| 2002/0022284 A1 | 2/2002 | Heeger | |
| 2002/0025391 A1 | 2/2002 | Angelopoulos | |
| 2002/0053320 A1 | 5/2002 | Duthaler | |
| 2002/0056839 A1 | 5/2002 | Joo et al. | |
| 2002/0068392 A1 | 6/2002 | Lee et al. | |
| 2002/0130042 A1 | 9/2002 | Stiene | |
| 2002/0170897 A1 | 11/2002 | Hall | |
| 2002/0195644 A1 | 12/2002 | Dodabalapur et al. | |
| 2003/0059987 A1 | 3/2003 | Sirringhaus et al. | |
| 2003/0112576 A1 | 6/2003 | Brewer et al. | |
| 2003/0175427 A1 | 9/2003 | Loo et al. | |
| 2004/0002176 A1 | 1/2004 | Xu | |
| 2004/0013982 A1 | 1/2004 | Jacobson et al. | |
| 2004/0026689 A1 | 2/2004 | Bernds et al. | |
| 2004/0084670 A1 | 5/2004 | Tripsas et al. | |
| 2004/0211329 A1 | 10/2004 | Funahata et al. | |

FOREIGN PATENT DOCUMENTS

| | | |
|---|---|---|
| DE | 4243832 | 6/1994 |
| DE | 19852312 | 5/1999 |
| DE | 19816860 | 11/1999 |
| DE | 19918193 | 11/1999 |
| DE | 10006257 | 9/2000 |
| DE | 19921024 | 11/2000 |
| DE | 19933757 | 1/2001 |
| DE | 69519782 | 1/2001 |
| DE | 19935527 | 2/2001 |
| DE | 19937262 | 3/2001 |
| DE | 10012204 | 9/2001 |
| DE | 10033112 | 1/2002 |
| DE | 100 45 192 | 4/2002 |
| DE | 100 47 171 | 4/2002 |
| DE | 10043204 | 4/2002 |
| DE | 100 58 559 | 5/2002 |
| DE | 10061297 | 6/2002 |
| DE | 101 17 663 | 10/2002 |
| DE | 101 20 687 | 10/2002 |
| DE | 10219905 | 12/2003 |
| EP | 0 128 529 | 12/1984 |
| EP | 0 268 370 A2 | 5/1988 |
| EP | 0 268 370 A3 | 5/1988 |
| EP | 0 350 179 | 1/1990 |
| EP | 0442123 | 8/1991 |
| EP | 0460242 | 12/1991 |
| EP | 0501456 A2 | 9/1992 |
| EP | 0501456 A3 | 9/1992 |
| EP | 0511807 | 11/1992 |
| EP | 0528662 | 2/1993 |
| EP | 0685985 | 12/1995 |
| EP | 0716458 | 6/1996 |
| EP | 0 785 578 A2 | 7/1997 |
| EP | 0 785 578 A3 | 7/1997 |
| EP | 0 615 256 B1 | 9/1998 |
| EP | 0962984 | 12/1999 |
| EP | 0966182 | 12/1999 |
| EP | 0979715 | 2/2000 |
| EP | 0981165 | 2/2000 |
| EP | 0989614 A2 | 3/2000 |
| EP | 1 052 594 | 11/2000 |
| EP | 1048912 | 11/2000 |
| EP | 1065725 A2 | 1/2001 |
| EP | 1065725 A3 | 1/2001 |
| EP | 1 083 775 | 3/2001 |
| EP | 1 102 335 A2 | 5/2001 |
| EP | 1 104 035 A2 | 5/2001 |
| EP | 1103916 | 5/2001 |
| EP | 1 134 694 | 9/2001 |
| EP | 1224999 | 7/2002 |
| EP | 1237207 | 9/2002 |
| EP | 1 318 084 | 6/2003 |
| FR | 2793089 | 11/2000 |
| GB | 723598 | 2/1955 |

| | | |
|---|---|---|
| GB | 2 058 462 | 4/1981 |
| JP | 54069392 | 6/1979 |
| JP | 60117769 | 6/1985 |
| JP | 61001060 | 1/1986 |
| JP | 61167854 | 7/1986 |
| JP | 362065477 A | 3/1987 |
| JP | 01169942 | 7/1989 |
| JP | 05152560 | 6/1993 |
| JP | 05259434 | 10/1993 |
| JP | 05347422 | 12/1993 |
| JP | 08197788 | 8/1995 |
| JP | 09083040 | 3/1997 |
| JP | 09320760 | 12/1997 |
| JP | 10026934 | 1/1998 |
| JP | 2969184 B | 11/1999 |
| JP | 2001085272 | 3/2001 |
| WO | WO9316491 | 8/1993 |
| WO | WO9417556 | 8/1994 |
| WO | WO 95/06240 | 3/1995 |
| WO | WO95/31831 | 11/1995 |
| WO | WO9602924 | 2/1996 |
| WO | WO 96/19792 | 6/1996 |
| WO | WO 97/12349 | 4/1997 |
| WO | WO9718944 | 5/1997 |
| WO | WO9818156 | 4/1998 |
| WO | WO9818186 | 4/1998 |
| WO | WO9840930 | 9/1998 |
| WO | WO9907189 | 2/1999 |
| WO | WO9910929 | 3/1999 |
| WO | WO9910939 | 3/1999 |
| WO | WO9921233 | 4/1999 |
| WO | WO9940631 | 8/1999 |
| WO | WO 99/53371 | 10/1999 |
| WO | WO9954936 | 10/1999 |
| WO | WO 99/66540 | 12/1999 |
| WO | WO 00/33063 | 6/2000 |
| WO | WO0036666 | 6/2000 |
| WO | WO0079617 | 12/2000 |
| WO | WO 01/03126 | 1/2001 |
| WO | WO 01/06442 | 1/2001 |
| WO | WO0108241 | 2/2001 |
| WO | WO 01/17029 | 3/2001 |
| WO | WO0115233 | 3/2001 |
| WO | WO0117041 | 3/2001 |
| WO | WO0127998 | 4/2001 |
| WO | WO 01/46987 | 6/2001 |
| WO | WO0147044 A2 | 6/2001 |
| WO | WO0147044 A3 | 6/2001 |
| WO | WO0147045 | 6/2001 |
| WO | WO 01 73109 A2 | 10/2001 |
| WO | WO 01 73109 A3 | 10/2001 |
| WO | WO0173109 A2 | 10/2001 |
| WO | WO0173109 A3 | 10/2001 |
| WO | WO 02/05360 | 1/2002 |
| WO | WO0205361 | 1/2002 |
| WO | WO 02/15264 | 2/2002 |
| WO | WO0219443 | 3/2002 |
| WO | WO 02/29912 | 4/2002 |
| WO | WO 02/43071 | 5/2002 |
| WO | WO0247183 | 6/2002 |
| WO | WO02065557 A1 | 8/2002 |
| WO | WO 02/071139 | 9/2002 |
| WO | WO 02/071505 | 9/2002 |
| WO | WO 02/076924 | 10/2002 |
| WO | WO 02/091495 | 11/2002 |
| WO | WO02095805 A2 | 11/2002 |
| WO | WO02095805 A3 | 11/2002 |
| WO | WO 02/099908 | 12/2002 |
| WO | WO 02099907 | 12/2002 |
| WO | WO 03/046922 | 6/2003 |
| WO | WO 03/069552 | 8/2003 |
| WO | WO03067680 | 8/2003 |
| WO | WO 03/081671 | 10/2003 |
| WO | WO 03/095175 | 11/2003 |
| WO | WO 2004/032257 | 4/2004 |
| WO | WO 2004/042837 | 5/2004 |
| WO | WO2004042837 | 5/2004 |
| WO | WO2004007194 A2 | 6/2004 |
| WO | WO2004007194 A3 | 6/2004 |
| WO | WO2004047144 A2 | 6/2004 |
| WO | WO2004047144 A3 | 6/2004 |
| WO | WO 2004/083859 | 9/2004 |

OTHER PUBLICATIONS

Bao, Z. et al., "High-Performance Plastic Transistors Fabricatecd by Printing Techniques", Chem. Mater vol. 9, No. 6, 1997, pp. 1299-1301.

Braun D., et al, "Visible light emission from semiconducting polymer diodes", American Institute of Physics, Applied Physics Letters 58, May 6, 1991, pp. 1982-1984.

Brown, A.R. et al., "Field-effect transistors made from solution-processed organic semiconductors", Elsevier Science, S.A., Synthetic Metals 88 (1997) pp. 37-55.

Brown, A.R., "Logic Gates Made from Polymer Transistors and Their Use in Ring Oscillators", Science, vol. 270, Nov. 10, 1995, pp. 972-974.

Chen, Shiao-Shien et al:, "Deep Submicrometer Double-Gate Fully-Depleted SOI PMOS Devices: A Concise Short-Channel Effect Threshold Voltage Model Using a Quasi-2D Approadh", IEEE Transaction on Electron Devices, vol. 43, No. 9, Sep. 1996.

Chen, X.L. et al., "Morphological and Transistor Studies of Organic Molecular Semiconductors with Anisotropic Electrical Characteristics", American Chemical Society, 2001, Chem. Mater. 2001, 13, 1341-1348.

Clemens, W. et al., "Vom Organischen Transistor Zum Plastik-Chip," Physik Journal, V. 2, 2003, pp. 31-36.

Collet J. et al:, Low Voltage, 30 NM Channel Length, Organic Transistors With a Self-Assembled Monolayer as Gate Insulating Films:, Applied Physics Letters, American Institute of Physics. New York, US, Bd 76, Nr. 14, Apr. 3, 2000, Seiten 1941-1943, XP000950589, ISSN:0003-6951, das ganze Dokument.

Crone, B. et al, "Large-scale complementary Integrated circuits based on Organic transistors", Nature, vol. 403, Feb. 3, 2000, pp. 521-.

Dai, L. et al, Photochemical Generation of Conducting Pattersn in Polybutadiene Films:, Macromolecules, vol. 29, No. 1, 1996, pp. 282-287, XP 001042019, the whole document.

De Leeuw D.M. et al., "Polymeric integrated circuits and light-emitting diodes", Electron Devices Meeting, 1997. Technical Digest, International, Washington, DC, USA Dec. 7-10, 1997, New York, NY, USA, IEEE, US Dec. 7, 1997.

Dodabalapur, A. et al., Organic smart pixels, American Institute of Physics, Applied Physics Letters, vol. 73, No. 2, Jul. 13, 1998, pp. 142-144.

Ficker, J. et al., "Dynamic and Lifetime Measurements of Polymer OFETS and Integrated Plastic Circuits," Proc. Of SPIE, v. 466, 2001, pp. 95-102.

Fix, W. et al., "Fast Polymer Integrated Circuits Based on a Polyfluorene Derivative", ESSDERC 2002, 2002, pp. 527-529.

Fix, W., et al., "Fast polymer integrated circuits", American Institute of Physics, Applied Physics Letters, vol. 81, No. 89, Aug. 2002, pp. 1735-1737.

Fraunhofer Magazin- Polytnonic Chips Von der Rolle, Apr. 2001, pp. 8-13.

Garnier F et al:, "Vertical Devices Architecture By Molding Of Organic-Based Thin Film Transistor", Applied Physics Letters, American Institute Of Physics. XP000784120, issn: 0003-6951 abbildung 2.

Garnier et al., "Conjugated Polymers and Oligomers as Active Material For Electronic Devices", Synthetic Metals, vol. 28, 1989.

Gelinck, G.H. et al., "High-Performance All-Polymer Integrated Circuits", Applied Physics Letters, v. 77, 2000, pp. 1487-1489.

Halls, J.J. M., et al., "Efficient photodiodes from interpenetrating polymer networks", Nature, vol. 376, Aug. 10, 1995, pp. 498-500.

Harsanyi G. et al, "Polytronics for biogtronics:unique possibilities of polymers in biosensors and BioMEMS", IEEE Polytronic 2002 Conference, Jun. 23, 2002, pp. 211-215.

Hebner, T.R. et al., Ink-jet printing of doped polymers for organic light emitting devices:, American Institute of Physics, Applied Physics Letters, vol. 72, No. 5, Feb. 2, 1998, pp. 519-521.

Hwang J D et al:, "A Vertical Submicron Sic thin film transistor", Solid State Electronics, Elsevier Science Publishers, Barking, GB, Bd. 38, NR. 2,Feb. 1, 1995, Seiten 275-278, XP004014040, ISSN:0038-1101, Abbildung 2.

IBM Technical Disclosure Bulletin, "Short-Channel Field-Effect Transistor", IBM Corp., New York, US, Bd. 32, Nr. 3A, Aug. 1, 1989, Seiten 77-78, XP000049357, ISSN:0018-8689, das ganze Dokument.

Klauk, H. et al., "Fast Organic Thin Film Transistor Circuits", IEEE Electron Device Letters, vol. 20, No. 6, pp. 289-291.

Klauk, H. et al., "Pentacene Thin Film Transistors and Inverter Circuits", 1997 International Exectron Devices Meeting Technical Digest, pp. 539-542, Dec. 1997.

Knobloch, A. et al., "Printed Polymer Transistors", Proc. Polytronic, v. 84, 2001, pp. 84-89.

Kobel W. et al., "Generation of Micropatterns in Poly (3-Methyl-Thiophene) Films Using Microlithography: A First Step in the Design of an All-Organic Thin-Film Transistor" Synthetic Metals, V. 22, 1988, pp. 265-271.

Kumar, Anish et al:, "Kink-Free Polycrystalline Silicon Double-Gate Elevated-Channel Thin-Film Transistors", IEEE Transactions on Electron Devices, vol. 45, No. 12, Dec. 1998.

Lidzey, D. G. et al., "Photoprocessed and Micropatterned Conjugated Polymer LEDs", Synthetic Metals, V. 82, 1996, pp. 141-148.

Lowe, J. et al., "Poly (3-(2-Acetoxyethyl)Thiophene): A Model Polymer for Acid-Catalyzed Lithography", Synthetic Metals, Elsevier Sequoia, Lausanne, CH, Bd. 85, 1997, Seiten 1427-1430.

Lucent Technologies, "Innovation marks significant milestone in the development of electronic paper", Cambridge, MA and Murray Hill, NJ, Nov. 20, 2000. XP-002209726.

Manuelli, Alessandro et al., "Applicability of Coating Techniques for the Production of Organic Field Effect Transistors", IEEE Polytronic 2002 Conference, 2002, pp. 201-204.

Miyamoto, Shoichi et al:, Effect of LDD Structure and Channel Poly-Si Thinning on a Gate-All-Around TFT (GAT) for SRAM's, IEEE Transactions on Electron Devices. vol. 46, No. 8, Aug. 1999.

Oelkrug, D. et al., "Electronic spectra of self-organized oligothiophene films with 'standing' and 'lying' molecular units", Elsevier Science S.A., 1996, Thin Solid Films 284-270.

Redecker, M. et al., "Mobility enhancement through homogeneous nematic alignment of a liquid-crystalline polyfluorene", 1999 American Institute of Physics, Applied Physics Letters, vol. 74, No. 10, pp. 1400-1402.

Rogers J A et al:, "Low-Voltage 0.1 Mum Organic Transistors and Complementary Inverter Circuits Fabricated with a Low-Cost Form of Near-Field Photolithography", Applied Physics Letters, American Institute of Physics. New York, US, Bd. 75, Nr. 7, Aug. 16, 1999, Seiten 1010-1012, XP000934355, ISSN: 003-6951, das ganze Dokument.

Rogers, J. A. et al:, "Printing Process Suitable for Reel-to-Reel Production of High-Performance Organic Transistors and Circuits", Advanced Materials, VCH, Verlagsgesellschaft, Weinheim, DE, Bd. 11, Nr. 9, Jul. 5, 1999, Seiten 741-745, P000851834, ISSN: 0935-9648, das ganze Dokument.

Roman et al., Polymer Diodes With High Rectification:, Applied Physics Letters, vol. 75, No. 21, Nov. 22, 1999.

Rost, Henning et al., "All-Polymer Organic Field Effect Transistors", Proc. Mat. Week, CD, 2001, pp. 1-6.

Sandberg, H. et al, "Ultra-thin Organic Films for Field Effect Transistors", SPIE vol. 4466, 2001, pp. 35-43.

Schoebel, "Frequency Conversion with Organic-On-Inorganic Heterostructured Diodes", Extended Abstracts of the International Conference on Solid State Devices and Materials, Sep. 1, 1997.

Schrodner M. et al., "Plastic electronics based on Semiconducting Polymers", First International IEEE Conference on Polymers and Adhesives in Microelectronics and Photonics. Incorporating Poly, Pep & Adhesives in Electronics. Proceedings (Cat. No. 01TH8592), First International IEEE Conference on Polymers and Adhesives in Micr, Seitenn 91-94.

Ullman, A. et al., "High Performance Organic Field-Effect Transistors and Integrated Inverters", Mat. Res. Soc. Symp. Proc., v. 665, 2001. pp. 265-270.

Vu, G. et al., "Dual-function semiconducting polymer devices: Light-emitting and photodetecting diodes", American Institute of Physics, Applied Physics Letter 64, Mar. 21, 1994, pp. 1540-1542.

Zheng, Xiang-Yang et al., "Electrochemical Patterning of the Surface of Insulators with Electrically Conductive Polymers", J. Electrochem. Soc., v. 142, 1995, pp. L226-L227.

U.S. Appl. No. 10/344,926, filed Feb. 12, 2004, Adolf Bernds et al.
U.S. Appl. No. 10/344,951, filed Feb. 12, 2004, Adolf Bernds et al.
U.S. Appl. No. 10/362,932, filed Oct. 2, 2003, Adolf Bernds et al.
U.S. Appl. No. 10/380,113, filed Sep. 25, 2003, Adolf Bernds et al.
U.S. Appl. No. 10/381,032, filed Feb. 12, 2004, Adolf Bernds et al.
U.S. Appl. No. 10/433,959, filed Apr. 1, 2004, Adolf Bernds.
U.S. Appl. No. 10/433,961, filed Apr. 1, 2004, Wolfgang Clemens et al.
U.S. Appl. No. 10/451,108, filed May 13, 2004, Mark Giles et al.
U.S. Appl. No. 10/467,636, filed Nov. 4, 2004, Adolf Bernds et al.
U.S. Appl. No. 10/473,050, filed May 20, 2004, Adolf Bernds et al.
U.S. Appl. No. 10/479,234, filed Dec. 30, 2004, Adolf Bernds et al.
U.S. Appl. No. 10/479,238, filed Oct. 20, 2004, Adolf Bernds et al.
U.S. Appl. No. 10/492,922, filed Mar. 3, 2005, Erwann Buillet et al.
U.S. Appl. No. 10/492,923, filed Dec. 23, 2004, Wolfgang Clemens et al.

Brabec, C.J. et al, "Photoinduced FT-IR spectroscopy and CW-photocurrent measurements of conjugated polymers and fullerenes blended into a conventional polymer matrix", Solar Energy Materials and Solar Cells, 2000 Elsevier Science V.V., pp. 19-33.

Brabec, C.J. et al., "Photovoltaic properties of a conjugated polymer/methanofullerene composites embedded in a polystyrene matrix", Journal of Applied Physics, vol. 85, No. 9, 1999, pp. 6866-6872.

Gosain, D.P., "Excimer laser crystallized poly-Si TFT's on plastic substrates", Second International Symposium on Laser Precision Microfabrication, May 16-18, 2001, Singapore, vol. 4426, pp. 394-400.

Koezuka, H. et al., "Macromolecular Electronic Device", Mol. Cryst. Liq. Cryst. 1994, vol. 2555, pp. 221-230.

Lu, Wen et al., "Use of Ionic Liquids for π-Conjugated Polymer Electrochemical Devices", Science, vol. 297, 2002, pp. 983-987.

Shaheen, S.E., et al., "Low band-gap polymeric photovoltaic devices", Synthetic Metals, vol. 121, 2001, pp. 1583-1584.

Takashima, W. et al., Electroplasticity Memory Devices Using Conducting Polymers and Solid Polymer Electroylytes, Polymer International, Melbourne, 1992, pp. 249-253.

Velu, G. et al. "Low Driving Voltages and Memory Effect in Organic Thin-Film Transistors With A Ferroelectric Gate Insulator", Applied Physics Letters, American Institute of Physics, New York, vol. 79, No. 5, 2001, pp. 659-661.

Wang, Yading et al., "Electrically Conductive Semiinterpenetrating Polymer Networks of Poly(3-octylthiophene)", Macromolecules 1992, vol. 25, pp. 3284-3290.

Dai, L. et al., "Conjugation of Polydienes by Oxidants Other Than Iodine", Elsevier Science S.A., Synthetic Metals 86 (1997) 1893-1894.

Dai, L. et al., "$I_2$-Doping" of 1,4-Polydienes, Elsevier Science S.A., Synthetic Metals 69 (1995), pp. 563-566.

Kawase, T. et al., "Inkjet Printed Via-Hole Interconnections and Resistors for All-Polymer Transistor Circuits", Advanced Materials 2001, 13, No. 21, Nov. 2, 2001, pp. 1601-1605.

Qiao, X. et al., "The FeCI3-doped poly3-alkithiophenes) in solid state", Elsevier Science, Synthetic Metals 122 (2001) pp. 449-454.

"Polytronic: Chips Von Der Rolle", Fraunhofer Magazin, Nr. 4, 2001, pp. 8-12, Munich.

Harsanyi G. et al, "Polytronics for biotronics:unique possibilities of polymers in biosensors and BioMEMS", IEEE Polytronic 2002 Conference, Jun. 23, 2002, pp. 211-215.

U.S. Appl. No. 10/562,989, filed Jun. 29, 2006, Jurgen Ficker et al.
U.S. Appl. No. 10/52,869, filed Oct. 05/2006, Walter Fix et al.

U.S. Appl. No. 10/568,730, filed Feb. 8, 2007, Wolfgang Clemens et al.
U.S. Appl. No. 10/569,233, filed Jan. 25, 2007, Adolf Bernds et al.
U.S. Appl. No. 10/570,571, filed Jan. 11, 2007, Wolfgang Clemens et al.
U.S. Appl. No. 10/562,869, filed Oct. 5, 2006, Walter Fix et al.
U.S. Appl. No. 10/569,763, filed Aug. 16, 2007, Walter Fix et al.
U.S. Appl. No. 10/585,775, filed Jul. 30, 2009, Walter Fix.
U.S. Appl. No. 11/574,139, filed Mar. 13, 2008, Jurgen Ficker.
U.S. Appl. No. 10/498,610, filed Jun. 20, 2006, Walter Fix et al.
U.S. Appl. No. 10/508,640, filed May 29, 2007, Walter Fix et al.
U.S. Appl. No. 10/508,737, Adolf Bernds et al.
U.S. Appl. No. 10/517,750, Wolfgang Clemens et al.
U.S. Appl. No. 10/523,216, filed Feb. 2, 2006, Adolf Bernds et al.
U.S. Appl. No. 10/523,487, filed Apr. 13, 2006, Wolfgang Clemens et al.

U.S. Appl. No. 10/524,646, filed May 11, 2006, Walter Fix et al.
U.S. Appl. No. 10/533,756, filed Jun. 8, 2006, Wolfgang Clemens et al.
U.S. Appl. No. 10/534,678, filed Jun. 8, 2006, Wolfgang Clemens et al.
U.S. Appl. No. 10/535,448, filed Jun. 8, 2006, W. Clemens et al.
U.S. Appl. No. 10/535,449, filed Feb. 16, 2006, Walter Fix et al.
U.S. Appl. No. 10/541,815, filed Jun. 8, 2006, Axel Gerlt et al.
U.S. Appl. No. 10/541,956, filed Jun. 15, 2006, Wolfgang Clemens et al.
U.S. Appl. No. 10/541,957, filed Jul. 6, 2006, Walter Fix et al.
U.S. Appl. No. 10/543,561, filed Mar. 8, 2007, Wolfgang Clemens et al.
U.S. Appl. No. 10/542,678, filed Jul. 20, 2006, Adolf Bernds et al.
U.S. Appl. No. 10/542,679, filed Mar. 16, 2006, Adolf Bernds et al.

* cited by examiner

MEASURING APPARATUS USED FOR DETERMINING AN ANALYTE IN A LIQUID SAMPLE, COMPRISING POLYMER ELECTRONIC COMPONENTS

The invention relates to a measuring apparatus used for determining an analyte in a liquid sample, having the following apparatus components: a test element with a test field for applying the liquid sample, the test element experiencing a detectable modification due to the analyte to be determined, a detector which detects the modification and generates an electrical detector signal as a function of it, an evaluation circuit arranged downstream of the detector, which evaluates the detector signal to form a measurement result, a display device connected to the evaluation circuit for displaying the measurement result, and an electrical power supply for supplying electrical power to the electrical apparatus components.

Such a measuring apparatus which is known from U.S. Pat. No. 6,300,141 is formed on a support, for example with the shape and size of a credit card, and consists of a lower support part and a colored or transparent cover part, which may both be made of plastic and are connected together, for example adhesively bonded. Arranged between the support part and the cover part there are an electrochemical biosensor formed by the test element with the detector, the evaluation circuit consisting of a microprocessor with memory, the display device consisting for example of a liquid crystal display, an operating element and the electrical power supply consisting of a solar cell or battery. The test field for applying the liquid sample, which is contained in the cover part, communicates via a liquid path with the biosensor, the liquid path and the biosensor being formed either in the lower support part or on a separate chip, which is plugged onto the support. In order to determine a plurality of analytes in the liquid sample, a plurality of biosensors may be provided which are then connected via separate liquid paths to a test field for applying the liquid sample.

A comparable measuring apparatus with an electooptical biosensor is known from U.S. Pat. No. 5,580,794. This, inter alia, specifies ways of calibrating the measuring apparatus during or after its production.

The known card-shaped measuring apparatus allow straightforward analytical diagnoses in the fields of health, food and environment, the measurement result being readable directly from the card. The measurement result may furthermore be stored on the card and read out by an external reader. The card-shaped measuring apparatus may be a disposable article. Since the liquid path, and possibly the biosensor, are longer to be used after a measurement has been taken, the entire card-shaped measuring apparatus would need to be disposed of if the liquid path and the biosensor were formed on the card itself. However, this is not practicable for cost reasons when the measurements take place quite rarely, i.e. only a few times per year.

It is therefore an object of the invention to allow straightforward and conveniently manageable but also cost-affective determination of an analyte in a liquid sample.

As is known from Fraunhofer Magazine 4, 2001, pages 8 to 13, conductive or semiconductive plastics have for some time offered a way of inexpensively mass producing electronic components and circuits. Examples of these are film batteries, organic solar cells, displays made organic light emitting diodes (OLEDs) and integrated circuits made of (semi)conductive organic materials, for example polymers (integrated plastic circuits=IPCs). For this new technology, terms such as organic electronics, polymer electronics, polytronics, electronic plastics or conductive plastics are often used synonymously.

According to the invention, the aforementioned object is achieved in that at least some of the electrical apparatus components in the measuring apparatus of the type specified in the introduction are formed on the basis of polymer electronics. Preferably all of the electrical apparatus components are formed on the basis of polymer electronics. The measuring apparatus according to the invention can thereby be produced particularly inexpensively so that, for example, it is also viable as a single-use article for frequent, for example daily measurements. The apparatus components produced in polymer electronics may thus, for example, be applied on a flat support (card, film etc.) by printing technology, for example using polymers in solution (so-called electronic inks) Since printing and laminating technologies are also known for the production of electrochemical sensors (glucose sensors) the complete measuring apparatus can thereby be applied on the support in a single printing technology process. All the apparatus components of the measuring apparatus may in this case be integrated on a support, or provision may be made for the test field and the test element or the test field, the test element and the detector to be formed in a first apparatus unit, which can be coupled via an interface to a further apparatus unit which contains the other apparatus components. The apparatus components of the first apparatus unit are then formed on a separate and therefore replaceable support, for example, which can be fastened, for example plugged, onto the support having the other apparatus components.

The apparatus components of the measuring apparatus according to the invention preferably furthermore comprise a controller which controls the measurement process for determining the analyte. In order to activate the measurement process, the controller may have means which respond to the actuation of an operating element on the measuring apparatus, for example an operating button, the removal of a cover on the measuring apparatus or application of the liquid sample onto the test field. The cover may, for example, be a film which covers the measuring apparatus fully or locally, e.g. in the region of the test field and/or an electrooptical element (e.g. solar cell) and whose removal is detected electrically, e.g. by making or breaking a contact, or optically. The cover, which may furthermore seal the measuring apparatus at least in the region of the test field against environmental effects such as water vapor and/or oxygen, may consist of packaging for the complete measuring apparatus. In order to protect the test field and the polymer electronics against light, the cover is furthermore preferably opaque. If removal of the cover, for example film or coating, before the anticipated use of the measuring apparatus is not intended, then the cover is designed to be transparent at least locally, especially in the region of the display device and a solar cell used as an electrical power supply.

The controller furthermore preferably has means for preventing further measurement processes with the same test element, which precludes reuse or multiple use of a test element that has already been used. If the measuring apparatus has only a single test element, then the reuse protection relates to the complete measuring apparatus. If the measuring apparatus has a plurality of test elements, as explained in more detail below, then the reuse protection relates initially to each individual test element, and only to the measuring apparatus itself once all the test elements have been used.

In this context, the measuring apparatus preferably has display means which can be driven by the controller in order to display that the test element or measuring apparatus is unusable. The unusability applies after the test element has been used once, at the end of the relevant measurement process. Unusability may furthermore be established for a test element that has not yet been used, by detecting and evaluating predetermined parameters of the test element, for example its electrical conductance. The unusability may be displayed via the display device of the measuring apparatus. In order to be able to permanently display the unusability independently of the electrical power supply, the display may be made bistable, i.e. switchable between a displaying state and a nondisplaying state, with energy being required only for the switchover. As an alternative, for example, the display may result from a chemical reaction, which leads to a color change, being initiated at a position on the measuring device by electrochemical or electrothermal driving.

The electrical power supply may be a solar cell or battery, preferably also in polymer electronics. In the case of a battery, provision may be made to delay bringing the electrolyte in contact with the electrodes of the battery until manual actuation on the measuring apparatus, for example by pressing an operating field, tearing the packaging etc., so that the battery is not formed until immediately before the measuring apparatus is used, in order to avoid problems due to battery discharge in the period between manufacture of the measuring apparatus and its use. Since the measurement process takes place within a defined time, the electrical power supply preferably contains a chargeable storage capacitor, which provides the required energy on demand for the time of the measurement. The storage capacitor, for example a double layer capacitor (super cap or super capacitor) may, for example, be charged by the solar cell or the battery directly or via a voltage converter to a defined voltage. Once the intended charge state has been reached, the measurement may then be initiated automatically or at the instigation of the user, optionally after having displayed the charge state via the display device. The storage capacitor may also be charged externally via contacts and/or contactlessly, for example via inductive or capacitive coupling, so that the solar cell or battery may then be obviated.

In connection with the determination of selected analytes in blood, for example glucose or lactate, a pricking aid, in particular a needle or a spike, is preferably integrated in the measuring apparatus in order to obtain the blood sample. The pricking aid may in this case be arranged outside the test field or test fields, so that the blood drop has to be brought onto the test field after pricking. As an alternative, the pricking aid is arranged in or immediately by the test field, so that the blood drop reaches the test field directly with the pricking.

In order to allow multiple use of the measuring apparatus according to the invention, at least one further test element with a test field and a detector is advantageously provided, the detectors being connected via a selection circuit to the evaluation circuit. The selection circuit always selects only one of the detectors and joins it only for single use to the selection circuit and subsequently selects an as yet unused biosensor after the measurement has taken place. By virtue of multiple usability, the measuring apparatus according to the invention can be much more cost-effective and convenient for the user than an apparatus which can be used only once. The selection circuit, which may be part of the controller, then ensures that only a single as yet unused test element with its detector is ever connected to the evaluation circuit.

By suitable driving of the display device, it is possible to show the user the test field assigned to the respective currently usable test element and furthermore, after all the available test elements have been used, to display that the measuring apparatus is unusable. In order to protect the unused test fields, they may be covered with a cover to be removed before use, in particular a film, the absence of a cover indicating directly to the user those test fields which can no longer be used. The selection circuit may detect removed covers via detection means, for example a breakable electrical conductor loop, so that previously used test fields or even ones exposed inadvertently or due to damage of the covers can be precluded from further use. This may be done in that, whenever it detects for the first time that a film has been torn off, the selection circuit selects the assigned detector—if it has not yet been to selected—and precludes it from any further use after a predetermined period of time sufficient for the measurement, As an alternative or in addition, the selection circuit may have means which respond to the actuation of an operating element on the measuring apparatus, for example a control button, or application of the liquid sample on one of the test fields, and which select the assigned detector for the measurement if it has not yet been selected.

Furthermore, the test fields in the edge area of the flat support may be arranged in zones separated from one another by break lines, in which case each zone can be broken off from the support after the test field lying in it has been used. The test fields in the zones are then preferably arranged so that they are respectively covered by a neighboring zone and are made accessible only by breaking off this neighboring zone. The effect of this is that the test fields can only be used in a predetermined order. Here again, the selection circuit may detect the zones having been broken off via detection means, so as to identify the test fields which can still be used.

To explain the invention further, reference will be made below to the figures of the drawing; specifically.

Figure 1:
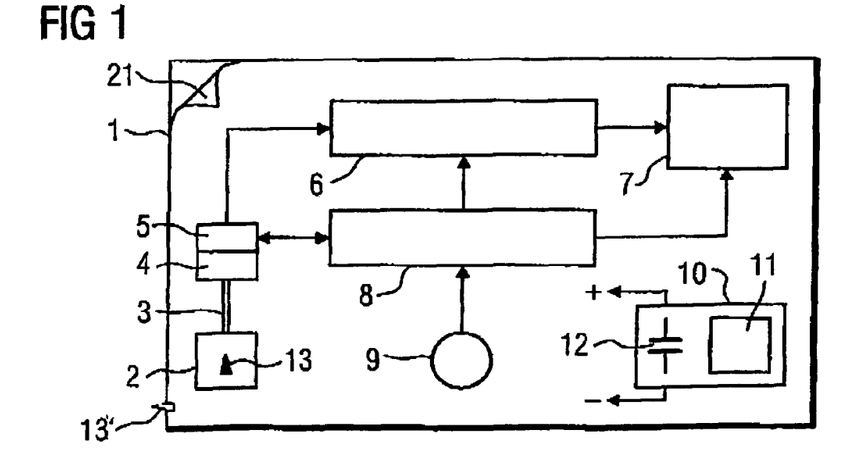
FIG. 1 shows a first exemplary embodiment of the measuring apparatus according to the invention with one test element as a simplified block diagram.

FIG. 1 shows a check card-shaped support 1 on which a test field 2 for applying a liquid sample is formed. The test field 2 communicates via a liquid path 3, or directly without intermediary, with a test element 4 which experiences a detectable modification due to the analyte to be determined. This modification is detected, for example optically or electrochemically, by means of a detector 5 which generates an electrical detector signal as a function of it. If the test element 4 has a biological or chemical component, for example an enzyme, an antibody or a microorganism, responsive to the analyte to be determined then the test sensor 4 and the detector 5 together form a so-called biosensor. Examples of such sensor structures are known from U.S. Pat. No. 5,997,817 or U.S. Pat. No. 6,036,919. If more than one analyte from the liquid sample is intended to be determined, then additional test elements with detectors are naturally provided and communicate with the test field 2.

The detector 5 is connected to an evaluation circuit 6, which evaluates the detector signal to form a measurement result and visualizes this by means of a display device 7. The measurement process is controlled by a controller 8 which, to this end, is connected to the detector 5, the evaluation circuit 6 and the display device 7. By an operating element 9 likewise connected to the controller 8, in the simplest case a single operating button, it is possible to perform the basic functions of the measuring apparatus, for example switching on and off, resetting, actuating an instruction shown on the display device 7 etc. The display device 7 may show the user the operating actions to be carried out in the form of text or pictograms, as well as the functional status of the measuring apparatus. The apparatus components 5 to 9 are supplied with electricity by an electrical power supply 10, preferably with a solar cell 11, which is for example arranged under the display device 7 to save space and can be illuminated by the ambient light passing through it. The electrical power supply 10 furthermore preferably contains a storage capacitor 12, which can be charged to a defined voltage from the solar cell 11 and which rapidly provides the energy required for the measurement process at a sufficient level on demand. All or at least some of the electrical apparatus components 5 to 12, for example with the exception of the electrical power supply 10 and/or the display device 7, are designed in polymer electronics and for example printed on a plastic support 1.

The support 1 with the apparatus components formed on it is covered with a cover 21, here in the form of a tear-off film, which protects the apparatus components 2 to 12 against environmental effects from the outside. The cover 21 may be opaque, which on the one hand provides light protection and, on the other hand, allows the solar cell 11 or another electooptical detector element (not shown here) to detect that the film 21 has been torn off before the measuring apparatus is used. If the cover 21 is intended to offer permanent protection even while the measuring apparatus is being used, then it is transparent at least in the region of the display device 7 and the solar cell 11, and has an opening in the region of the test field 2.

A pricking aid, here a spike 13, is integrated in the region of the test field 2 on the support 1 in order to obtain blood as the liquid sample. The spike 13 may, for example, be arranged under a blister cover over the test field 2, which yields to finger pressure against a mechanical prestress so that the spike 13 pricks the finger. As indicated by dashes the pricking aid 13', which may consist of the material of the card-shaped support 1, may also be arranged in the vicinity of the test field 2 as an alternative.

Figure 2:
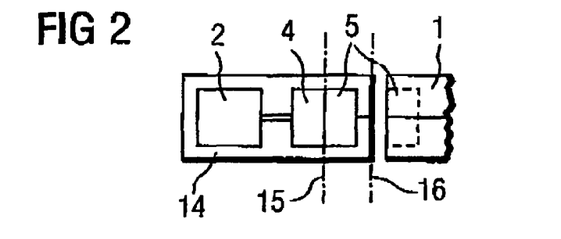
FIG. 2 shows modification of the exemplary embodiment according to FIG. 1.

As shown by FIG. 2, the test field 2 with the test element 4 and optionally the detector 5 may be formed on a separate support 14, which can be coupled via an interface 15 or 16 to the card-shaped support 1.

Figure 3:
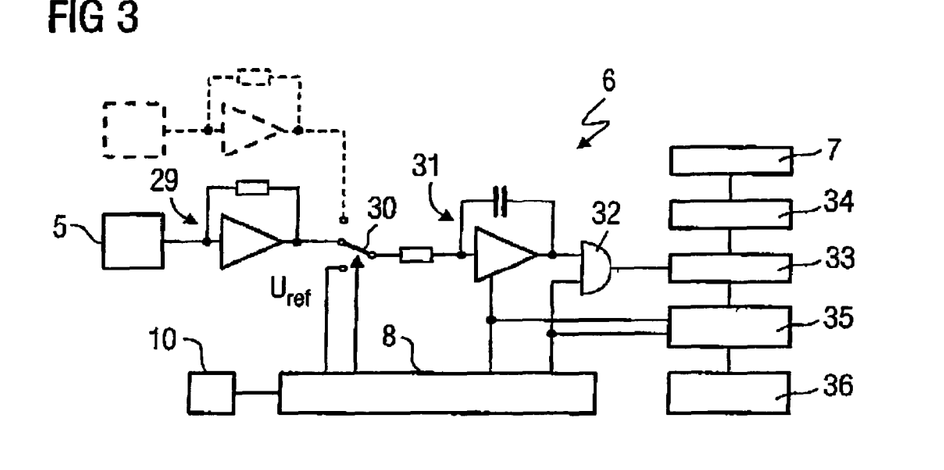
FIG. 3 shows a simplified example of the electrical circuit of the measuring apparatus according to the invention.

FIG. 3 shows an example of the electrical circuit of the measuring apparatus according to the invention. On the input side, the evaluation circuit 6 has an amplifier 29 which, depending on the nature of the detector 5 and the detector signal generated by it, amplifies its output voltage or converts the output current into a voltage. The voltage obtained in this way is delivered via a controllable switch 30 to an analog/digital converter (ADC) 31, here a dual slope ADC, which generates a digital serial measurement result. This measurement result is read via a gate 32 under clock control into a shift register 33, from which it is delivered via decoder logic 34 to the display device 7 where it is visualized. Using the controllable switch 30, the input of the analog/digital converter 31 can be connected to a reference voltage $U_{ref}$ which is provided here by the controller 8. The switch 30 may furthermore be used to select other detectors as indicated by dashes, as will be explained below with reference to FIG. 4. To this end, the controller 8 drives the switch 30 and also generates a reset signal for the analog/digital converter 31 and the clock signal for the gate 32.

Lastly, the controller 8 also controls the calibration of the measuring apparatus by correcting the digital measurement result contained in the shift register 33 by means of a computing instrument 35 on the basis of calibration data contained in a calibration data memory 36. The calibration data memory 36 may be a programmable memory (for example EEPROM), into which the calibration data are read via contacts and/or contactlessly, for example by means of a transponder, or it may be an electrical connection structure which can be electrothermally by means of a laser or otherwise. This is because it is necessary to carry out batch-specific calibration of the measuring apparatus owing to incompletely controllable production conditions. In general, this is done by testing the measuring apparatus after fabrication with the aid of reference samples with a known concentration and checking the reproduction of the known concentration in the measurement result. Owing to batch-specific variations, it may then be necessary to provide the measuring apparatus with calibration data by which the measurement results can be corrected. It is naturally possible to introduce the calibration even during the production of the measuring apparatus, by calibrating some of the measuring apparatus after their fabrication and entering the calibration data into the other measuring apparatus of the batch during their production.

Figure 4:
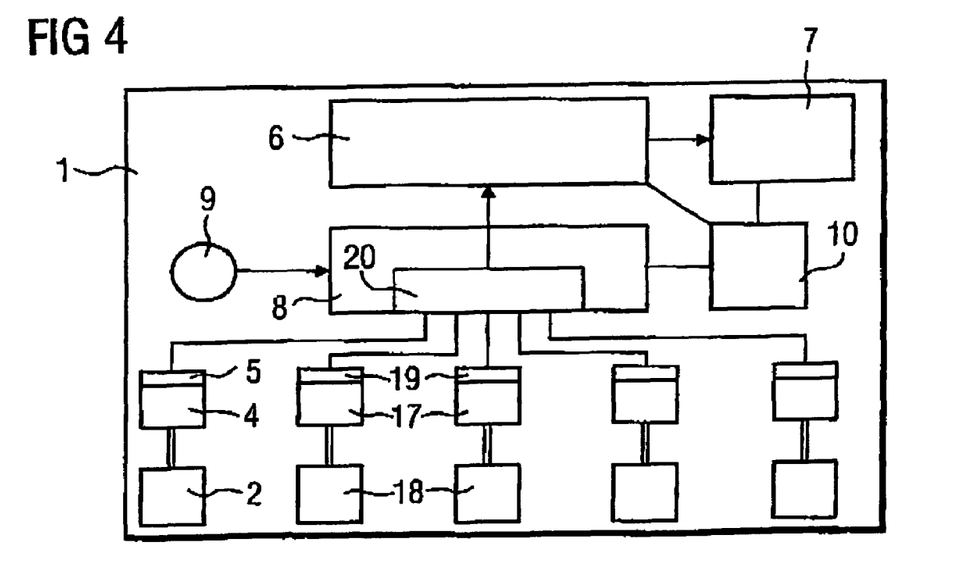
FIG. 4 shows another exemplary embodiment of the measuring apparatus according to the invention with a plurality of test elements as a simplified block diagram and FIGS. 5 to 8 show views of various exemplary embodiments of the measuring apparatus according to the invention.

In the exemplary embodiment shown in FIG. 4, further test elements 17 with test fields 18 and detectors 19 are formed on the card-shaped support 1, in addition to the test element 4 with the test field 2 and the detector 5. The detectors 19 are connected to a selection circuit 20, which is part of the controller 8 and always selects only one test element, specifically one which has not yet been used, connects the associated detector to the evaluation circuit 6 and, after the measurement has been carried out, selects an as yet unused test element for the next measurement. The evaluation circuit 6 evaluates the detector signal of the detector respectively connected to it, in order to form a measurement result which is visualized by means of the display device 7. The basic functions of the measuring apparatus can be performed by means of the operating element 9. The electrical apparatus components 5 to 9, 19 and 20 are supplied with electricity by the electrical power supply 10. Here again, at least some of the electrical apparatus components 5 to 10, 19 and 20 are designed in polymer electronics and for example printed on the plastic support 1.

Figure 5:
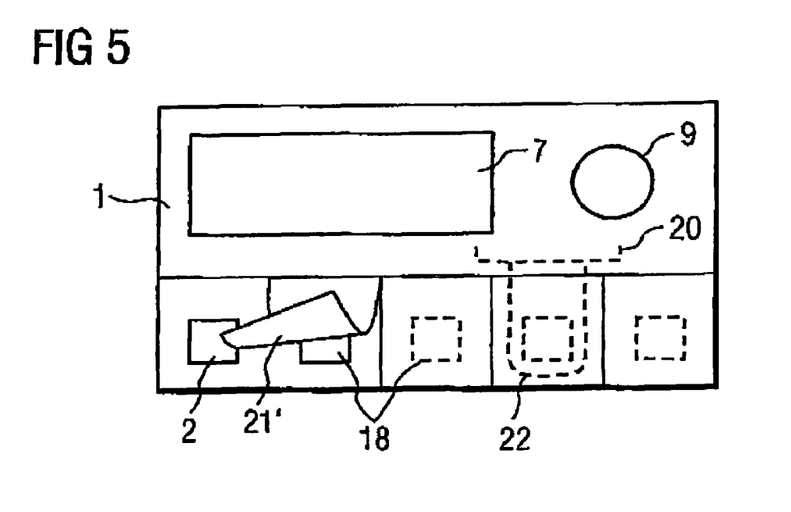

FIG. 5 shows the view of an exemplary embodiment of the measuring apparatus according to the invention, in which the support 1 with the test fields 2, 18, the display device 7 and the operating element 9 can be seen. The test fields 2, 18 are respectively covered by tear-off covers 21, here in the form of films. As can be seen with reference to the example of a film 21' assigned to one of the further test fields 18, detection means 22 are provided in the form of a breakable line loop etc. and signal to the selection circuit 20 as soon as a film has been removed or damaged. When a film 21' has been removed, the underlying test field with the assigned test element and the detector can be selected for the measurement over a predetermined period of time. After this period of time has elapsed and/or after the end of the measurement, the relevant test element is blocked for future selection and use.

Figure 6:
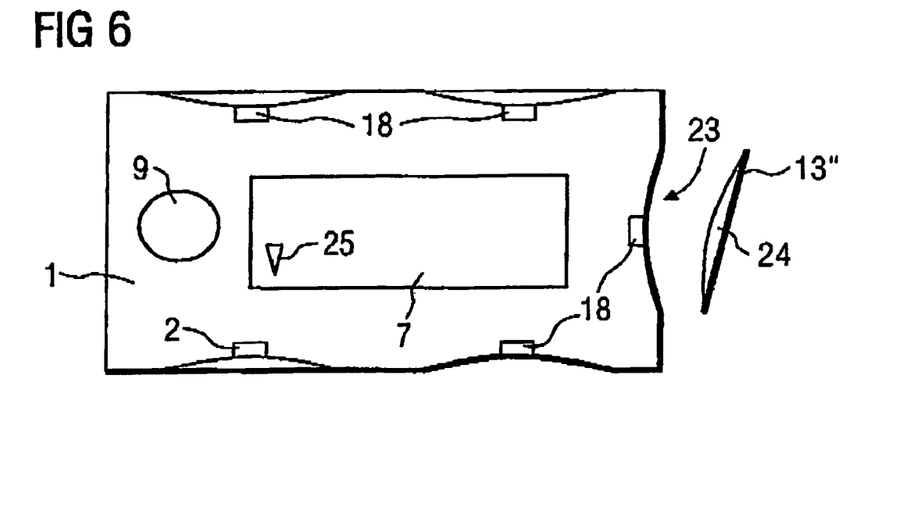

In the exemplary embodiment shown in FIG. 6, the test fields 2, 18 are designed as known from U.S. Pat. No. 5,997, 817, for example, and are arranged in trough-like recesses 23 at the edge of the card-shaped support 1 where they are protected by covers 24 which can be broken off. Those of the test fields 2, 18 which have already been used are immediately apparent to the user. The fact that the covers 24 have been broken off can be detected similarly as the tearing of the films 21' in the example according to FIG. 5. The display device 7 shows, here by an arrow 25, the test field e.g. 2 selected for the next use. As shown here, the covers 24 may be designed with sharp edges so that they can be used as a pricking aid 13" to take blood after breaking.

Figure 7:
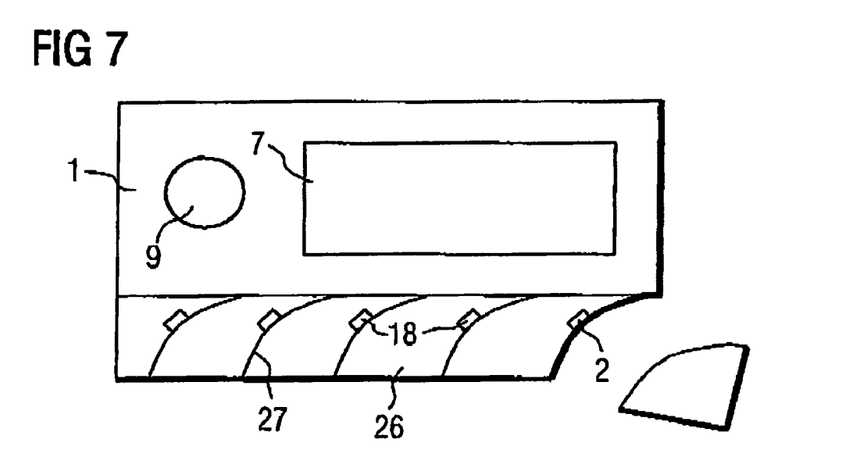

In the exemplary embodiment shown in FIG. 7, the test fields 2, 18 at the edge of the card-shaped support 1 are arranged in zones 26 which are separated from one another by break lines 27, so that the individual zones 26 can be broken off from the support 1 after having used the test fields, test elements and optionally detectors contained in them, and thus cannot be used again. So that this can be done effectively, the test fields 2, 18 are arranged in the regions of the break lines 27 respectively toward a neighboring zone 26, so that the test fields 2, 18 are not made accessible until after this neighboring zone has been broken off.

Figure 8:
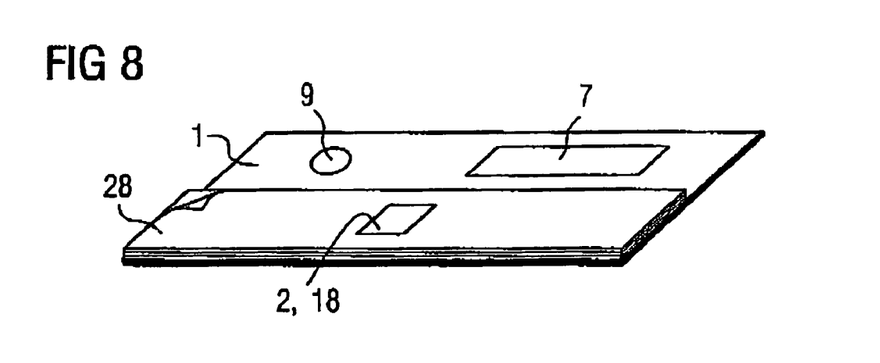

In the exemplary embodiment shown in FIG. 8, the test fields 2, 18 with the test elements and detectors (not shown here) are arranged on separate support films 28, which are applied above one another on the support 1 having the other apparatus components, e.g. 7 and 9. The support films 28 can be torn off one after the other, only the test field on the top support film 28 being usable in each case while the test fields lying below are protected. In order to electrically connect the detectors to the selection circuit on the support 1, the support films 28 are provided with contacts through to the support 1. The fact that support films 28 have been torn off may be detected electrically or optically, as explained above. As indicated by dashes, the support films 28 may extend over the entire area of the support 1, in which case they are transparent in the region of the display device 7 and the operating button 9.

The invention claimed is:

1. A disposable one piece measuring apparatus for determining an analyte in a liquid sample comprising: a one piece substrate; and on the substrate: a plurality of test elements; a plurality of test fields each corresponding to a different test element for applying the liquid sample to the different test element, the different test elements each experiencing a detectable modification due to the analyte to be determined in response to the applied sample; and a plurality of electrical components comprising: a detector which corresponds to each test field and test element and detects the modification and generates an electrical detector signal as a function of the detected modification; an evaluation circuit coupled to the detector to evaluate the detector signal and generate a measurement result; a display device connected to the evaluation circuit for displaying the measurement result; and an electrical power supply for supplying electrical power to the electrical components comprising the detector, evaluation circuit, and display device wherein at least a majority of the electrical components are formed on the basis of polymer electronics; wherein the test fields are arranged at an edge region of the substrate in zones separated from one another by break lines and in that each zone is arranged to be broken off from the substrate at the break lines after the test field lying in it has been used.

2. The measuring apparatus as claimed in claim 1 wherein the electrical components further comprise a controller which controls the determination of the analyte in a measurement process.

3. The measuring apparatus as claimed in claim 1 wherein the electrical components include a controller which controls the determination of the analyte wherein the controller includes an arrangement for activating the measurement process, which arrangement responds to at least one of the following events: an operating element on the measuring apparatus is actuated, a cover on the measuring apparatus is removed, and the liquid sample is applied onto the test field.

4. The measuring apparatus as claimed in claim 1 wherein the electrical components include a controller which controls the determination of the analyte wherein the controller includes an arrangement for preventing further measurement processes with the same test element.

5. The measuring apparatus as claimed in claim 1 wherein the electrical components include a controller which controls the determination of the analyte wherein the display device and controller are arranged to display that the measuring apparatus is unusable.

6. The measuring apparatus as claimed in claim 1 wherein the evaluation circuit includes a calibration data memory with calibration data for correcting the measurement results to be displayed.

7. The measuring apparatus as claimed in claim 1 wherein a pricking aid is coupled to the test field to obtain blood as the liquid sample.

8. The measuring apparatus as claimed in claim 1 wherein the detector comprises a plurality of detectors each corresponding to a different test field and that are connected via a selection circuit to the evaluation circuit and in that the selection circuit always selects only one of the detectors at a time and joins the selected one detector only for single use to the selection circuit and subsequently selects an as yet unused detector after the measurement has taken place.

9. The measuring apparatus as claimed in claim 8 wherein the substrate comprises a flat support.

10. The measuring apparatus as claimed in claim 9 wherein the detectors joined to the selection circuit are arranged in the regions of the break lines and in that the selection circuit detects zones having been broken off.

11. The measuring apparatus as claimed in claim 1 wherein the test fields are respectively covered with a corresponding cover to be removed before use, in that the detectors joined to a selection circuit are arranged in the regions of the covers and in that the selection circuit detects that the corresponding covers have been removed.

12. The measuring apparatus as claimed in claim 1 wherein the test fields are arranged in the zones so that they are respectively covered by a neighboring zone and are accessible only after this neighboring zone has been broken off.

13. A disposable one piece measuring apparatus for determining an analyte in a liquid sample comprising:
a substrate;
and on the substrate:
a plurality of test elements each with a corresponding test field for applying the liquid sample to the corresponding test element, the test elements each experiencing a detectable modification due to the analyte to be determined; and
a plurality of electrical components comprising:
a detector corresponding to each test element and its corresponding test field, which detector detects the modification and generates an electrical detector signal as a function of the detected modification on the corresponding test element;
an evaluation circuit coupled to the detector to evaluate the detector signal and generate a measurement result;
a display device connected to the evaluation circuit for displaying the measurement result;
a controller which controls the determination of the analyte; and
an electrical power supply for supplying electrical power to the electrical components comprising the tester, detector, evaluation circuit, controller and display device such that at least a majority of the electrical components are formed on the basis of polymer electronics;

the test fields being arranged at an edge region of the substrate in zones separated from one another by break lines and in that each zone is arranged to be broken off from the substrate at the break lines after the test field lying in it has been used.

14. A disposable one piece measuring apparatus for determining an analyte in a liquid sample comprising:

a substrate;

and on the substrate:

a plurality of test elements each with a corresponding test field for applying the liquid sample to the corresponding test element for determination of the analyte, the test elements each experiencing a detectable modification due to the analyte to be determined; and a plurality of electrical components comprising:

a detector corresponding to each test element and its corresponding test field, which detector detects the modification and generates an electrical detector signal as a function of the detected modification on the corresponding test element;

an evaluation circuit coupled to the detector to evaluate the detector signal and generate a measurement result;

a display device connected to the evaluation circuit for displaying the measurement result;

a controller which controls the determination of the analyte; and an electrical power supply for supplying electrical power to the electrical components comprising the tester, detector, evaluation circuit, controller and display device such that at least a majority of the electrical components are formed on the basis of polymer electronics;

wherein the test fields are located in zones which are individually removable from the substrate and arranged so that they are each respectively covered by a neighboring zone and are accessible for only after the neighboring zone has been removed.

15. The measuring apparatus of any one of claims 1, 13, or 14 wherein the detectors are connected via a selection circuit to the evaluation circuit such that the selection circuit always selects only one of the detectors and joins the selected one detectors only for single use to the selection circuit and subsequently selects an as yet unused detector after the measurement has taken place.

16. The measuring apparatus as claimed in claim 15 wherein the selection circuit is arranged to drive the display device, so that the display device displays the test field assigned to a currently usable detector, and wherein the test elements and the test fields are mounted on the substrate by break lines for selective separation of the corresponding test field from the substrate.

17. A disposable one piece measuring apparatus for determining an analyte in a liquid sample comprising: a one piece substrate; and on the substrate: a plurality of test elements; a plurality of test fields each corresponding to a different test element for applying the liquid sample to the different test element, the different test elements each experiencing a detectable modification due to the analyte to be determined in response to the applied sample; and a plurality of electrical components comprising: a detector which corresponds to each test field and test element and detects the modification and generates an electrical detector signal as a function of the detected modification; an evaluation circuit coupled to the detector to evaluate the detector signal and generate a measurement result; a display device connected to the evaluation circuit for displaying the measurement result; and an electrical power supply for supplying electrical power to the electrical components comprising the detector, evaluation circuit, and display device wherein at least a majority of the electrical components are formed on the basis of polymer electronics; wherein the test fields are located in zones which are individually removable from the substrate and arranged so that they are each respectively covered by a neighboring zone and are accessible only after the neighboring zone has been removed.

* * * * *

UNITED STATES PATENT AND TRADEMARK OFFICE
CERTIFICATE OF CORRECTION

| | | |
|---|---|---|
| PATENT NO. | : 7,641,857 B2 | Page 1 of 1 |
| APPLICATION NO. | : 10/534678 | |
| DATED | : January 5, 2010 | |
| INVENTOR(S) | : Wolfgang Clemens, Axel Gerlt and Bernd Roesicke | |

It is certified that error appears in the above-identified patent and that said Letters Patent is hereby corrected as shown below:

On the Title Pg. Item (75) change inventor's name Bernd "Rosicke" to Bernd -- Roesicke --

Signed and Sealed this

Twentieth Day of April, 2010

David J. Kappos
*Director of the United States Patent and Trademark Office*

UNITED STATES PATENT AND TRADEMARK OFFICE
CERTIFICATE OF CORRECTION

PATENT NO. : 7,641,857 B2  Page 1 of 1
APPLICATION NO. : 10/534678
DATED : January 5, 2010
INVENTOR(S) : Clemens et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1091 days.

Signed and Sealed this

Sixteenth Day of November, 2010

David J. Kappos
*Director of the United States Patent and Trademark Office*